United States Patent
Davis et al.

(10) Patent No.: US 6,352,862 B1
(45) Date of Patent: *Mar. 5, 2002

(54) ANALYTICAL TEST DEVICE FOR IMUNO ASSAYS AND METHODS OF USING SAME

(75) Inventors: Paul James Davis, Bedfordshire; Michael Evans Prior, Northamptonshire; Keith May, Bedfordshire, all of (GB)

(73) Assignee: Unilever Patent Holdings B.V., Rotterdam (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/871,641

(22) Filed: Jun. 9, 1997

Related U.S. Application Data

(63) Continuation of application No. 08/488,460, filed on Jun. 7, 1995, now abandoned, which is a continuation of application No. 08/400,500, filed on Mar. 8, 1995, now abandoned, which is a continuation of application No. 08/183,263, filed on Jan. 19, 1994, now abandoned, which is a continuation of application No. 07/585,066, filed on May 19, 1992, now abandoned.

(30) Foreign Application Priority Data

Feb. 17, 1989 (GB) ................................................ 8903627

(51) Int. Cl.$^7$ ................................................ G01N 33/53
(52) U.S. Cl. .................... 436/510; 422/55; 422/101; 436/518; 436/525; 436/528; 436/530; 436/541; 436/810; 436/814; 436/818; 435/7.92; 435/7.95; 435/805; 435/806; 435/810; 435/970
(58) Field of Search .............................. 435/7.92–7.95, 435/805, 806, 810, 970, 6; 436/518, 525, 528, 530, 541, 810, 814, 818; 422/101, 55

(56) References Cited

U.S. PATENT DOCUMENTS

| | | |
|---|---|---|
| 3,410,839 A | 11/1968 | De Carvalho |
| 3,420,205 A | 1/1969 | Morison |
| 3,437,449 A | 4/1969 | Luckey |

(List continued on next page.)

FOREIGN PATENT DOCUMENTS

| | | |
|---|---|---|
| AU | 6007486 | 7/1985 |
| CA | 1 185 882 | 11/1981 |
| CA | 1273306 | 8/1990 |

(List continued on next page.)

OTHER PUBLICATIONS

Carpenter et al, Elsevier Science Publishers B.V. (Biomedical Division), 1987.
Crowe et al, J. Biochem., 242:1–10 (1987).
Ikram et al, J. of Virological Methods, 13:143–148 (1986).

(List continued on next page.)

*Primary Examiner*—Lynette R. F. Smith
*Assistant Examiner*—Ginny Allen Portner
(74) *Attorney, Agent, or Firm*—Pillsbury Winthrop LLP

(57) ABSTRACT

An analytical test device incorporating a dry porous carrier to which a liquid sample, eg. urine, suspected of containing an analyte such as HCG or LH can be applied indirectly, the device also incorporating a labelled specific binding reagent which is freely mobile in the porous carrier when in the moist state, and an unlabelled specific binding reagent which is permanently immobilised in a detection zone on the carrier material, the labelled and unlabelled specific binding reagents being capable of participating in either a sandwich reaction or a competition reaction in the presence of the analyte, in which prior to the application to the device of a liquid sample suspected of containing the analyte, the labelled specific binding reagent is retained in the dry state in a macroporous body, eg. of plastics material having a pore size of 10 microns or greater, through which the applied liquid sample must pass en route to the porous carrier material, the labelled specific binding reagent being freely soluble or dispersible in any liquid sample which enters the macroporous body.

21 Claims, 2 Drawing Sheets

U.S. PATENT DOCUMENTS

| | | |
|---|---|---|
| 3,475,129 A | 10/1969 | Peurifoy et al. |
| 3,620,677 A | 11/1971 | Morison |
| 3,666,421 A | 5/1972 | Price |
| 3,720,760 A | 3/1973 | Bennich et al. |
| 3,723,064 A | 3/1973 | Liotta |
| 3,744,975 A | 7/1973 | Mailen |
| 3,798,004 A | 3/1974 | Zerachia et al. |
| 3,811,840 A | 5/1974 | Bauer |
| 3,850,578 A | 11/1974 | McConnell |
| 3,876,504 A | 4/1975 | Koffler |
| 3,915,647 A | 10/1975 | Wright |
| 3,981,981 A | 9/1976 | Reunanen |
| RE29,169 E | 4/1977 | Schuurs et al. |
| 4,016,043 A | 4/1977 | Schuurs et al. |
| 4,018,662 A | 4/1977 | Ruhenstroth-Bauer et al. |
| 4,022,876 A | 5/1977 | Anbar |
| 4,042,335 A | 8/1977 | Clement |
| 4,087,326 A | 5/1978 | Kereluk |
| 4,087,332 A | 5/1978 | Hansen |
| 4,094,647 A | 6/1978 | Deutsch et al. |
| 4,116,638 A | 9/1978 | Kenoff |
| 4,120,945 A | 10/1978 | Gutcho et al. |
| 4,122,030 A | 10/1978 | Smith et al. |
| 4,123,173 A | 10/1978 | Bullock et al. |
| 4,133,639 A | 1/1979 | Harte |
| 4,145,186 A | 3/1979 | Andersen |
| 4,166,102 A | 8/1979 | Johnson |
| 4,166,105 A | 8/1979 | Hirschfeld |
| 4,168,146 A | 9/1979 | Grubb et al. |
| 4,169,138 A | 9/1979 | Jonsson |
| 4,180,383 A | 12/1979 | Johnson |
| 4,191,533 A | 3/1980 | Bohn et al. |
| 4,219,335 A | 8/1980 | Ebersole |
| 4,225,558 A | 9/1980 | Peterson et al. |
| 4,230,683 A | 10/1980 | Decker |
| 4,233,029 A | 11/1980 | Columbus |
| 4,233,286 A | 11/1980 | Soothill et al. |
| 4,237,234 A | 12/1980 | Meunier |
| 4,244,916 A | 1/1981 | Guigan |
| 4,244,940 A | 1/1981 | Jeong et al. |
| 4,248,965 A | 2/1981 | Mochida et al. |
| 4,256,724 A | 3/1981 | Rutner et al. |
| 4,256,725 A | 3/1981 | Rutner et al. |
| 4,258,001 A | 3/1981 | Pierce et al. |
| 4,267,270 A | 5/1981 | Stout |
| 4,270,921 A | 6/1981 | Graas |
| 4,274,832 A | 6/1981 | Wu et al. |
| 4,278,651 A | 7/1981 | Haler |
| 4,279,862 A | 7/1981 | Bretaudiere et al. |
| 4,279,885 A | 7/1981 | Reese et al. |
| 4,298,345 A | 11/1981 | Sodickson et al. |
| 4,301,139 A | 11/1981 | Feingers et al. |
| 4,302,536 A | 11/1981 | Longenecker |
| 4,313,734 A | 2/1982 | Leuvering |
| 4,315,908 A | 2/1982 | Zer |
| 4,323,536 A | 4/1982 | Columbus |
| 4,326,008 A | 4/1982 | Rembaum |
| 4,332,783 A | 6/1982 | Pernice et al. |
| 4,338,094 A | 7/1982 | Elahi |
| 4,347,312 A | 8/1982 | Brown et al. |
| 4,363,874 A | 12/1982 | Greenquist |
| 4,366,241 A | 12/1982 | Tom et al. |
| 4,373,812 A | 2/1983 | Stein et al. |
| 4,373,932 A | 2/1983 | Gribanau et al. |
| 4,374,925 A | 2/1983 | Litman et al. |
| 4,380,580 A | 4/1983 | Boguslaski et al. |
| 4,411,518 A | 10/1983 | Meserol etal. |
| 4,425,438 A | 1/1984 | Bauman et al. |
| 4,427,779 A | 1/1984 | Recket et al. |
| 4,435,504 A | 3/1984 | Zuk |
| 4,442,204 A | 4/1984 | Greenquist et al. |
| 4,444,193 A | 4/1984 | Fogt et al. |
| 4,446,232 A | 5/1984 | Liotta |
| 4,447,526 A | 5/1984 | Rupchock et al. |
| 4,452,901 A | 6/1984 | Gordon |
| 4,454,226 A | 6/1984 | Ali et al. |
| 4,457,916 A | 7/1984 | Hayashi et al. ............. 424/101 |
| 4,461,829 A | 7/1984 | Greenquist |
| 4,469,787 A | 9/1984 | Woods |
| 4,474,878 A | 10/1984 | Halbert et al. |
| 4,483,921 A | 11/1984 | Cole |
| 4,483,928 A | 11/1984 | Suzuta et al. |
| 4,483,929 A | 11/1984 | Szoka |
| 4,493,793 A | 1/1985 | Chu |
| 4,503,143 A | 3/1985 | Gerber et al. |
| 4,515,889 A | 5/1985 | Klose et al. |
| 4,517,288 A | 5/1985 | Giegel et al. |
| 4,518,565 A | 5/1985 | Boyer et al. |
| 4,526,871 A | 7/1985 | Avrameas et al. |
| 4,552,839 A | 11/1985 | Gould |
| 4,554,256 A | 11/1985 | Sasser et al. |
| 4,587,102 A | 5/1986 | Nugatomo et al. |
| 4,590,170 A | 5/1986 | Akiyoshi et al. |
| 4,592,338 A | 6/1986 | Blackmore |
| 4,594,327 A | 6/1986 | Zuk |
| 4,595,656 A | 6/1986 | Allen et al. |
| 4,608,246 A | 8/1986 | Bayer et al. |
| 4,650,769 A | 3/1987 | Kakimi et al. |
| 4,656,129 A | 4/1987 | Wagner |
| 4,659,678 A | 4/1987 | Forrest et al. |
| 4,666,866 A | 5/1987 | Krauth |
| 4,668,638 A | 5/1987 | Janoff et al. |
| 4,670,406 A | 6/1987 | Allen et al. |
| 4,678,757 A | 7/1987 | Rapkin |
| 4,693,970 A | 9/1987 | O'Connell et al. |
| 4,695,554 A | 9/1987 | O'Connell |
| 4,703,017 A | 10/1987 | Campbell et al. |
| 4,713,249 A | 12/1987 | Schruder |
| 4,727,019 A | 2/1988 | Valkirs .......................... 435/5 |
| 4,740,468 A | 4/1988 | Weng et al. |
| 4,742,011 A | 5/1988 | Blake et al. |
| 4,743,560 A | 5/1988 | Campbell et al. |
| 4,757,002 A | 7/1988 | Joo |
| 4,762,857 A | 8/1988 | Bollin, Jr. et al. .......... 514/777 |
| 4,774,192 A | 9/1988 | Terminiello et al. ........ 436/530 |
| 4,775,515 A | 10/1988 | Cottingham |
| 4,803,170 A | 2/1989 | Stanton et al. |
| 4,806,311 A | 2/1989 | Greenquist |
| 4,806,312 A | 2/1989 | Greenquist |
| 4,810,470 A | 3/1989 | Burkhardt |
| 4,837,145 A | 6/1989 | Liotta |
| 4,837,168 A | 6/1989 | de Jaenger et al. |
| 4,849,337 A | 7/1989 | Calenoff et al. |
| 4,851,356 A | 7/1989 | Canfield et al. |
| 4,855,240 A | 8/1989 | Rosenstein et al. |
| 4,857,453 A | 8/1989 | Ullman et al. |
| 4,861,552 A | 8/1989 | Masuda et al. |
| 4,861,711 A * | 8/1989 | Friesen et al. ............ 422/56 X |
| 4,868,106 A | 9/1989 | Ito et al. ........................ 435/7 |
| 4,868,108 A | 9/1989 | Buher et al. |
| 4,874,710 A | 10/1989 | Piran |
| 4,889,816 A | 12/1989 | Davis |
| 4,891,313 A | 1/1990 | Berger et al. ................... 436/7 |
| 4,891,319 A | 1/1990 | Roser ......................... 435/188 |
| 4,891,324 A | 1/1990 | Pease ......................... 436/519 |
| 4,900,663 A | 2/1990 | Wie et al. |
| 4,904,583 A | 2/1990 | Mapes et al. |
| 4,906,439 A | 3/1990 | Grenner |
| 4,916,056 A | 4/1990 | Brown |
| 4,938,927 A | 7/1990 | Kelton et al. |
| 4,943,522 A | 7/1990 | Eisenger et al. ................ 435/7 |

| | | |
|---|---|---|
| 4,954,452 A | 9/1990 | Yost et al. |
| 4,956,275 A | 9/1990 | Zuk et al. |
| 4,956,302 A | 9/1990 | Gordon |
| 4,960,691 A | 10/1990 | Gordon et al. ............... 435/6 |
| 4,963,468 A | 10/1990 | Olson ........................... 435/7 |
| 4,978,504 A | 12/1990 | Nason ......................... 422/61 |
| 4,981,786 A | 1/1991 | Duppoin et al. |
| 4,999,285 A | 3/1991 | Stiso |
| 5,026,653 A | 6/1991 | Lee et al. |
| 5,030,558 A | 7/1991 | Litman et al. |
| 5,073,340 A | 12/1991 | Covington |
| 5,073,484 A | 12/1991 | Swanson |
| 5,075,078 A * | 12/1991 | Osikowicz et al. ........... 422/56 |
| 5,078,968 A | 1/1992 | Nason ......................... 422/58 |
| 5,079,142 A | 1/1992 | Coleman et al. |
| 5,079,174 A * | 1/1992 | Buck et al. .................... 422/56 |
| 5,089,394 A | 2/1992 | Chun |
| 5,114,673 A | 5/1992 | Berger et al. ................. 422/56 |
| 5,120,643 A * | 6/1992 | Ching et al. ............... 435/7.92 |
| 5,141,875 A | 8/1992 | Keltron et al. |
| 5,160,701 A * | 11/1992 | Brown, III et al. ......... 435/7.12 |
| 5,202,268 A | 4/1993 | Kuhn et al. ................. 436/525 |
| 5,206,177 A * | 4/1993 | DeLaCroix et al. ....... 435/7.12 |
| 5,217,405 A * | 6/1993 | Marchand et al. ......... 435/7.12 |
| 5,591,645 A | 1/1997 | Rosenstein |
| 5,602,040 A | 2/1997 | May et al. |
| 5,622,871 A | 4/1997 | May et al. |
| 5,656,503 A | 8/1997 | May et al. |
| 5,714,389 A | 2/1998 | Charlton et al. ............ 436/514 |
| 5,766,933 A | 6/1998 | El Shami et al. ......... 435/287.2 |
| 5,783,401 A | 7/1998 | Toledano .................... 435/7.9 |
| 5,958,790 A | 9/1999 | Cerny ......................... 436/501 |
| 5,989,921 A | 11/1999 | Charlton et al. ............ 436/501 |
| 6,020,147 A | 2/2000 | Guire et al. ............... 435/7.92 |
| 6,187,598 B1 | 2/2001 | May et al. |

FOREIGN PATENT DOCUMENTS

| | | | |
|---|---|---|---|
| EP | 63810 | 11/1982 | |
| EP | 97952 | 11/1984 | |
| EP | 125 118 | 11/1984 | |
| EP | 0 140 489 | 5/1985 | |
| EP | 0 212 603 | 8/1985 | |
| EP | 0 154 749 | 9/1985 | |
| EP | 158746 | 10/1985 | |
| EP | B10174247 | 3/1986 | |
| EP | A30174247 | 3/1986 | |
| EP | 0 183 442 | 6/1986 | |
| EP | 186 100 | 7/1986 | |
| EP | 0 186 799 | 7/1986 | |
| EP | 0 191 640 | 8/1986 | |
| EP | 0 199 205 | 10/1986 | |
| EP | 0 212 599 | 3/1987 | |
| EP | 0 238 012 | 9/1987 | |
| EP | 0 249 418 | 12/1987 | |
| EP | 0 250 137 | 12/1987 | |
| EP | 253 581 | 1/1988 | |
| EP | 0255342 | 2/1988 | |
| EP | 0291194 | 4/1988 | |
| EP | 0 277 723 | 8/1988 | |
| EP | 0 279 097 | 8/1988 | |
| EP | 279 097 | 8/1988 | |
| EP | 0281201 | 9/1988 | |
| EP | 0 284 232 | 9/1988 | |
| EP | 0286371 | 10/1988 | |
| EP | 0291194 | 11/1988 | ................ 436/518 |
| EP | 0 299 359 | 1/1989 | |
| EP | 0 299 428 | 1/1989 | |
| GB | 1526708 | 9/1978 | |
| GB | 2 016 687 | 9/1979 | |
| GB | 2 986 041 | 5/1982 | |
| GB | 2111676 | 7/1983 | |
| GB | 2 204 398 A | 11/1988 | |
| JP | 485925 | 1/1973 | |
| JP | 536465 | 2/1978 | |
| JP | 59122950 | 7/1984 | |
| WO | WO8001515 | 7/1980 | |
| WO | WO8102790 | 10/1981 | |
| WO | WO-8603839 | 7/1986 | |
| WO | WO 86/04683 | 8/1986 | |
| WO | WO 87/00196 | 1/1987 | |
| WO | WO 87/02774 | 5/1987 | |
| WO | WO 89/06799 | 7/1989 | |

OTHER PUBLICATIONS

Ansari et al, J. Immunological Methods, 84:117–124 (1985).
Hellman et al, Biochirmica As Biophysica Acta, 749:133–142 (1983).
Arakawa et al, Biochemistry, 21:6536–6544 (1982).
Lee et al, J. of Biological Chemistry, 256(14):7193–7201 (19981).
Carpenter et al, International Symposium on Biological Product Freeze–Drying and Formulation (1990).
Obringer et al, J. of Immunological Methods, 185:81–93 (1995).
Yoshioka et al, J. of Chromatography, 566:361–368 (1991).
Blanchard et al, J. of Immunological Methods, 130:263–275 (1990).
Miller III et al, J. of immunological Methods, 125:35–40 (1989).
Eckerskorn et al, Eur. J. Biochem, 176:509–519 (1988).
Aebersold et al, J. of Biological Chemistry, 261(9):4229–4238 (1986).
Vanderkerckhove et al, Eur. J. Biochem., 152:9–19 (1985).
Kato et al, J. Biochem, 82:261–266 (1977).
Jones, IVD Technology 32, (1999).
Kato et al, J. Biochem, 82:261–266 (1977).
Kenna, et al., "Methods for Reducing Non–Specific Antibody Binding in Enzyme–Linked Immunosorbent Assays", Journal of Immunological Methods, 85 (1985) pp. 409–419.
Vogt, Jr. et al., "Quantitative differences among various proteins as blocking agents for ELISA microtiter plates", Journal of Immunological Methods, 101 (1987) pp. 43–50.
Romano et al., "An Antiglobulin Reagent Labelled With Colloidal Gold For Use In Electron Microscopy", Immunochemistry, 1974, vol. 11, pp. 521–522.
Glad et al, Analytical Biochemistry (B5) 1978, pp. 180–187.
Gribnau et al, J. Chromatography 376 (1986) pp. 175–189.
Leuvering et al, "Optimization of a Sandwich Sol Particle Immunoassay for Human Chlorionic Gonadotrophin", J. of Immunological Methods, 2:175–184, (1982).
J. Sharon et al. Detection of . . . Antibodies, Proc. Nat. Acad. Sci. USA., 76, pp. 1420–1424, (1979).
G.B. Wisdom, "Enzyme–Immunoassay", Clinical Chemistry, 22, 1248–1255, 1976.
Micheel et al, "A Solid–Phase . . . Filters", Acta Histochem, vol. 71, pp. 15–18 (1982).
Hawkes et al, "A Dot–Immunobinding Assay . . . Antibodies", Analytical Biochemistry, vol. 119, pp. 142–147 (1982).
Esen et al, "A Simple and Rapid . . . Prolamins", Analytical Biochemistry, vol. 132, pp. 462–467 (1983).
Bennett et al, "An improved Procedure . . . Supernatants", Journal of Immunological Methods, vol. 61, pp. 201–207 (1983).
Norgaard–Pedersen, "A Highly Sensitive . . . α–Fetoprotein", Clin. Chem. Acta, vol. 48, pp. 345–346, (1973).

Langone et al. "Immunochemical Techniques", Methods In Enzymology, vol. 73, pp. 339–348, (1981).

Syva/a Syntex Co., AccuLevel TDM Assays, Pamphlet, pp. 1–6, (1987).

T.C.J. Gribnau et al, "Affinity Chromatography . . . Techniques", Elsevier Scientific Pub. Co., pp. 411–424, (1982).

Laurell et al, "Electroimmunoassay", Academic Press, vol. 73, pp. 339, 340, 346–348 (1981).

Frens, G., Nature Physical Science, "Controlled Nucleation for the Regulation of the Particle Size in Monodisperse Gold Suspensions", vol. 241, Jan. 1, 1973, pp. 1–3.

Hoye, Age, "Determination of Radiochemical . . . High-–Voltage Electrophoresis", Journal of Chromatography, 28 (1967), pp. 379–384.

Hsu, "Immunogold for Detection of Antigen on Nitrocellulose Paper", Analytical Biochemistry, vol. 142, (1984), pp. 221–225.

Surek et al., "Visualization Of Antigenic . . . Method", Biochemical and Biophysical Research Communications, vol. 121, May 1, 1984, pp. 284–289.

Geoghegan et al., "Passive Gold . . . Hemagglutination", Journal of Immunological Methods, 34, (1980), pp. 11–21.

R. Brdicka, "Grundlagen Der Physikalischen Chemie", Berlin 1958, pp. 775, 784–787, (and English translation).

Zsigmondy, "Ueber wassrige Losungen metallischen goldes", Annalen der Chemie, 301 (1898), pp. 28–55, (and English translation).

Sahlbom, Kolloichemische Beihefte, Band II, (1910–1911), pp. 78–141, (and English translation).

Zuk, et al. "Enzyme Immunochromatography—A Quantitative Immunoassay Requiring No Instrumentation", Clinical Chemistry, vol. 31, No. 7, 1985, pp. 1144–1150.

Van Hell, et al., "Particle immunoassays", Chapter 4, Alternative Immunoassays, Collins, (1985) pp. 39–58.

Bosch, M.G., "Enzym–und Sol Particle Immunoassays for Hormone,", Archives of Gynecology and Obstetrics, vol. 242, No. 1–4, (1987), pp. 509–512 (and English translation).

Moecremans, et al., "Sensitive Visualization . . . Straining", Journal of Immunological Methods, 74 (1984) pp. 353–360.

Leuvering, et al., "Sol Particle Immunoassay (SPIA)", Abstract, Journal Of Immunoassay, 1 (1), pp. 77–91 (1980).

Leuvering, et al., "Optimization of a Sandwich Sol . . . Gonadotrophin", Journal of Immunological Methods, 62 (1983), pp. 175–184.

* cited by examiner

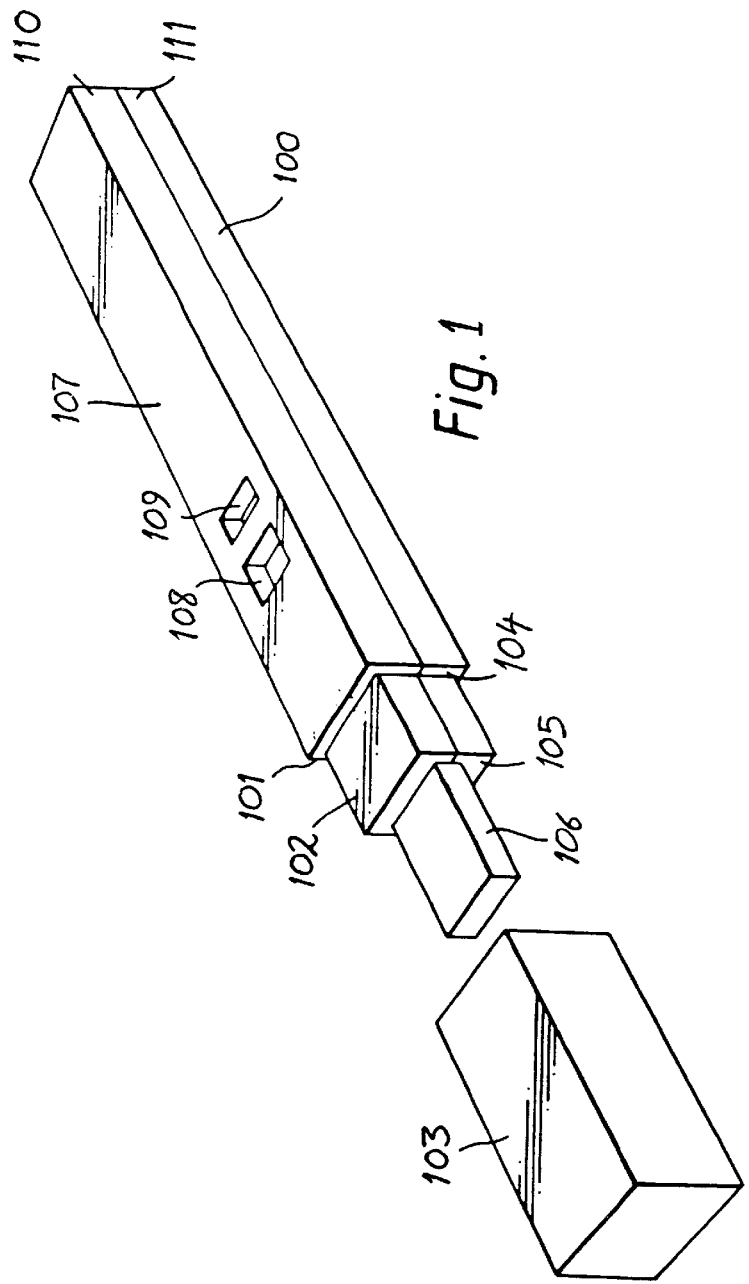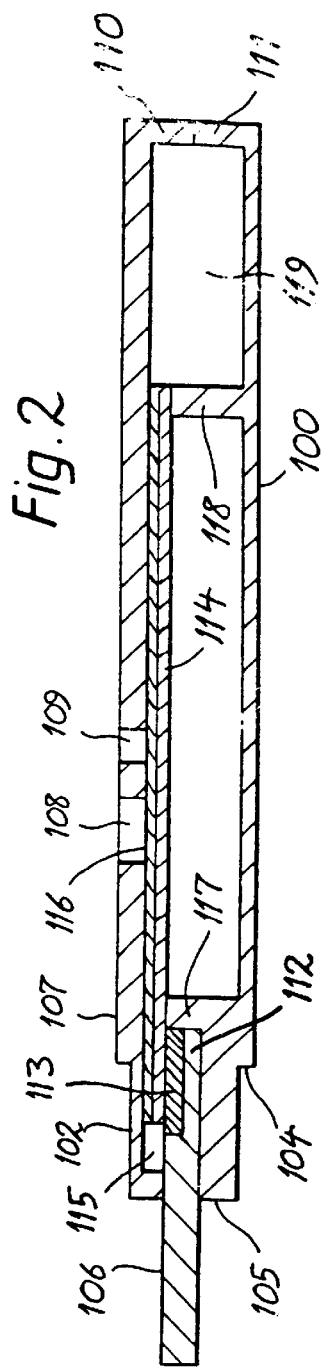

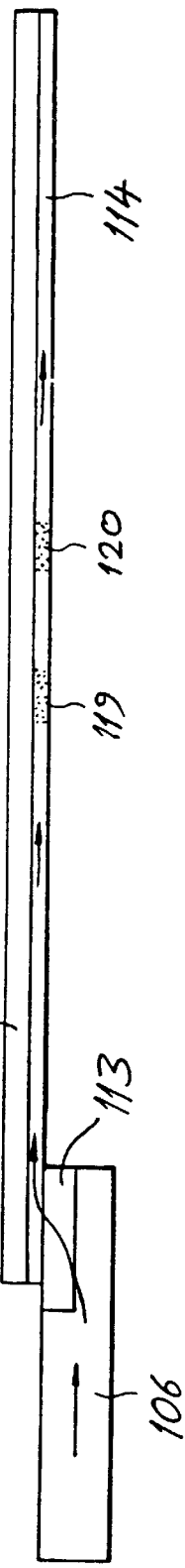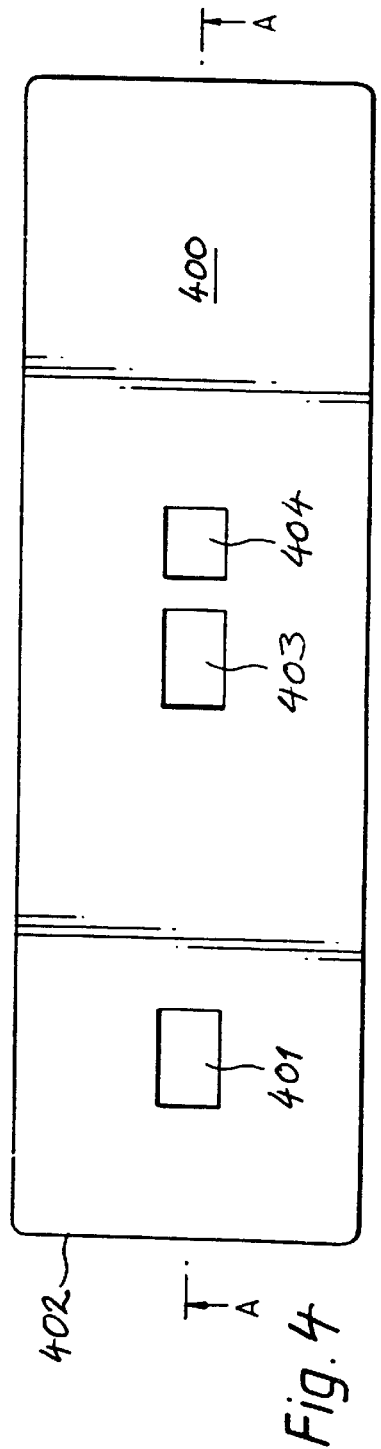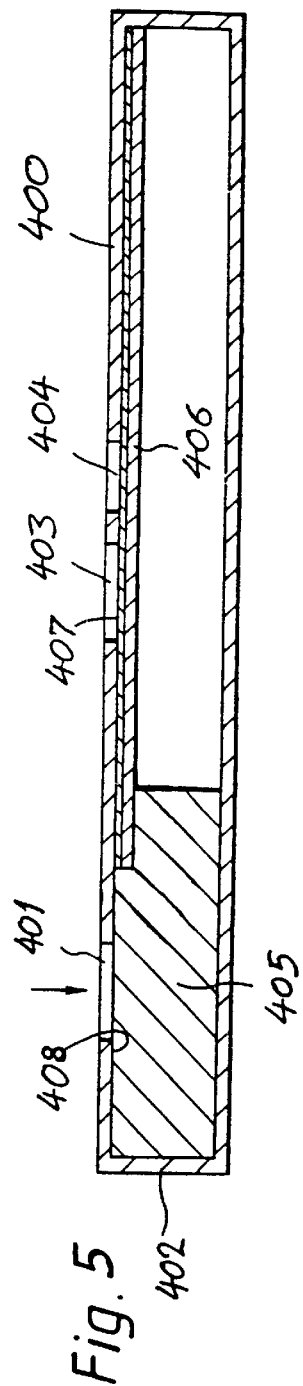

ANALYTICAL TEST DEVICE FOR IMUNO ASSAYS AND METHODS OF USING SAME

This is a continuation of application Ser. No. 8/488,460, filed on Jun. 7, 1995, which was abandoned upon the filing hereof; a cont. of application Ser. No. 08/400,500 filed Mar. 8, 1995, abandoned; which is a cont. of application Ser. No. 08/183,263 filed Jan. 19, 1994, now abandoned; which was a cont. of application Ser. No. 07/585,066 filed May 19, 1992, now abandoned.

FIELD OF THE INVENTION

The present invention relates to assays involving specific binding, especially immunoassays.

In particular, the invention relates to analytical devices which are suitable for use in the home, clinic or doctor's surgery and which are intended to give an analytical result rapidly and which require the minimum degree of skill and involvement from the user. The use of test devices in the home to test for pregnancy and fertile period (ovulation) is now commonplace.

BACKGROUND PRIOR ART TO THE INVENTION

In the specification of UK patent application GB 2204398A we describe test devices which are readily usable even by an unskilled person and which typically merely require that some portion of the device is contacted with a sample (e.g. urine in the case of a pregnancy or ovulation test) and thereafter no further actions are required by the user before an analytical result can be observed. The analytical result can be observable within a matter of minutes following sample application, e.g. ten minutes or less.

The use of reagent-impregnated test strips in specific binding assays, such as immunoassays, has previously been proposed. In such procedures a sample is applied to one portion of the test strip and is allowed to permeate through the strip material, usually with the aid of an eluting solvent such as water. In so doing, the sample progresses into or through a detection zone in the test strip wherein a specific binding reagent is immobilised. Analyte present in the sample can participate in a sandwich or a competition reaction within the detection zone, with a labelled reagent which can also be incorporated in the test strip or applied thereto. Examples of prior proposals utilising these principles are given in Thyroid Diagnostics Inc GB 1589234, Boots-Celltech Diagnostics Limited EP 0225054, Syntex (USA) Inc EP 0183442, and Behringwerke AG EP 0186799.

SUMMARY OF THE INVENTION

The present invention provides an analytical test device incorporating a dry porous carrier to which a liquid sample suspected of containing an analyte can be applied indirectly, the device also incorporating a labelled specific binding reagent which is freely mobile in the porous carrier when in the moist state, and an unlabelled specific binding reagent which is permanently immobilised in a detection zone on the carrier material, the labelled and unlabelled specific binding reagents being capable of participating in either a sandwich reaction or a competition reaction in the presence of the analyte, in which prior to the application to the device of a liquid sample suspected of containing the analyte, the labelled specific binding reagent is retained in the dry state in a macroporous body through which the applied liquid sample must pass en route to the porous carrier material, the labelled specific binding reagent being freely soluble or dispersible in any liquid sample which enters the macroporous body.

The invention also encompasses a macroporous body containing in the dry state a labelled specific binding reagent that is freely soluble or dispersible in an aqueous sample that may be applied to the macroporous body. The invention further encompasses any analytical device that incorporates such a macroporous body together with a test strip or the like into which liquid sample carrying dissolved or dispersed labelled specific binding reagent can flow from the macroporous body. The invention also encompasses the use of such a macroporous body to facilitate the uptake of a labelled specific binding agent by a liquid sample before such a sample is analysed on a test strip or the like.

BRIEF DESCRIPTION OF THE DRAWINGS

FIG. 1 represents an isometric view of an assay device in accordance with the invention;

FIG. 2 represents a cross-sectional side elevation of the device shown in FIG. 1.

FIG. 3 shows an enlarged view of the sample collector, macroporous body and test strip in the device illustrated in FIGS. 1 and 2.

FIGS. 4 and 5 illustrate another embodiment of the invention, which is seen in plan view in FIG. 4 and in cross-section in FIG. 5, the cross-section being an elevation on the line A seen in FIG. 4.

Preferably, the dry porous carrier material comprises a chromatographic strip, such as a strip of nitrocellulose. If desired, the nitrocellulose can be backed with moisture impermeable material, such as polyester sheet. Using nitrocellulose as the porous carrier material has considerable advantage over more conventional strip materials, such as paper, because nitrocellulose has a natural ability to bind proteins without requiring prior sensitisation. Specific binding reagents, such as immunoglobulins, can be applied directly to nitrocellulose and immobilised thereon. No chemical treatment is required which might interfere with the essential specific binding activity of the reagent. Unused binding sites on the nitrocellulose can thereafter be blocked using simple materials, such as polyvinylalcohol. Moreover, nitrocellulose is readily available in a range of pore sizes and this facilitates the selection of a carrier material to suit particularly requirements such as sample flow rate. Preferably the nitrocellulose has a pore size of at least one micron. Preferably the nitrocellulose has a pore size not greater than about 20 microns.

In a preferred embodiment of the invention, the labelled specific binding reagent comprises a specific binding reagent attached to a particulate label. Such "direct labels", e.g. coloured latex particles, gold sols, non-metallic colloids, and dye sols, are already known per se. They can be used to produce an instant analytical result without the need to add further reagents in order to develop a detectable signal. They are robust and stable and can therefore be used readily in a analytical device which is stored in the dry state. Their release on contact with an aqueous sample can be modulated, for example by the use of soluble glazes. Preferably, the particulate label is a latex particle, such as a coloured latex particle which can be readily visible to the eye if it becomes bound in the detection zone. If desired, the assay result can be read instrumentally, eg. by colour reflectance. Alternatively, the latex particle can incorporate a fluorescent compound which can respond to applied electromagnetic energy such as ultraviolet light or visible light, to provide an emitted signal that can be measured instrumentally. In a particularly preferred embodiment, the direct label is a coloured latex particle of spherical or near-spherical shape and having a maximum diameter of not greater than about 0.5 micron. An ideal size range for such particles is from about 0.05 to about 0.5 microns.

We have found that use of a macroporous body as the portion of the device wherein the applied liquid sample encounters the particulate label considerably facilitates the ease with which the particulate label is taken up by the liquid sample, compared to the situation that usually prevails if the particulate label is incorporated as a pre-dosed reagent on the dry porous carrier strip. To enable the particulate label to migrate freely out of the macroporous body with the liquid sample, the macroporous body preferably has a pore size at least 10 times greater than the maximum particle size of the particulate label. More preferably, the macroporous body comprises plastics material having an average pore size of not less than 10 microns, and ideally about 100 microns, because such larger pore sizes give better release of the labelled reagent. The plastics material should not be protein-binding, or should be easily blockable by means of reagents such as BSA or PVA, to minimise non-specific binding and to facilitate free movement of the labelled reagent after the macroporous body has become moistened with the liquid sample. The plastics material can be pre-treated with surface active agent or solvent, if necessary, to render it more hydrophilic and to promote rapid uptake of the liquid sample. Alternatively, if desired, a surface active agent can be incorporated in the solution containing the labelled reagent when this is applied to the macroporous material during manufacture of the device.

The labelled reagent is preferably incorporated in the macroporous material in bulk, eg. large sheet, form before it is subdivided into individual bodies for use in a testing device of the invention.

After a solution containing the labelled reagent has been allowed to saturate the macroporous material, the macroporous material should be dried, eg. by vacuum or air-drying, or preferably by freeze-drying. Optionally, the solution can also contain a surface active agent, such as a detergent, and/or a glazing material, such as a sugar, e.g. sucrose. The presence of the glazing material appears to enhance release of the labelled reagent and promotes stability of delicate specific binding reagents such as antibodies.

By incorporating the labelled reagent in a separate macroporous body, rather than pre-dosed onto the carrier material that also incorporates the detection zone, the following advantages can be obtained:

Enhanced sensitivity of the test, because a substantial quantity of the liquid sample is able to take up the labelled reagent before migrating through the carrier material to the detection zone, enhancing potential reaction time without significantly increasing overall test time. Also, the liquid which permeates the carrier is of a more uniform and consistent composition. Whereas the test devices as described in our earlier patent application GB 2204398A are primarily, although not exclusively, suited to qualitative assays, those of the present invention are especially suitable for quantitative assays as well as for qualitative assays.

Enhanced perceived performance of the test. For example, when the device incorporates a carrier strip and the detection zone comprises a line of immobilised reagent, and the label is a visible direct label, a positive result shows up more clearly, with much reduced temporary background caused by the visible labelled reagent being progressively conveyed past the detection zone.

Ease of manufacture, because the incorporation of the labelled reagent in the separate macroporous body avoids the need to apply the labelled reagent in a special zone in the carrier, which may need careful pre-treatment, as described in our GB 2204398A.

If the assay device is intended to identify more than one analyte in a single sample, the macroporous body can incorporate several labelled specific binding reagents each carrying a different label, eg. having different colours or fluorescent properties. This will facilitate the manufacture of a multiple analyte testing device.

Ideally, the macroporous body is in direct moisture-conductive contact with the porous material, and the detection zone on the porous carrier material is spaced away from the region of contact between the porous carrier material and the macroporous body. In such an embodiment, the quantity of liquid sample required to saturate the macroporous body is preferably not less than the quantity of liquid sample capable of being absorbed by the mass of porous carrier material linking the macroporous body and the detection zone. In other words, the liquid capacity of the macroporous body is at least equal to the liquid capacity of the working portion of the porous carrier.

The invention also provides an analytical method in which a device as set forth above is contacted with an aqueous liquid sample suspected of containing the analyte, such that the sample permeates by capillary action via the macroporous body through the porous solid carrier into the detection zone and the labelled reagent migrates therewith to the detection zone, the presence of analyte in the sample being determined by observing the extent (if any) to which the labelled reagent becomes bound in the detection zone.

In one embodiment of the invention, the labelled reagent is a specific binding partner for the analyte. The labelled reagent, the analyte (if present) and the immobilised unlabelled specific binding reagent cooperate together in a "sandwich" reaction. This results in the labelled reagent being bound in the detection zone if analyte is present in the sample. The two binding reagents must have specificities for different epitopes on the analyte.

In another embodiment of the invention, the labelled reagent is either the analyte itself which has been conjugated with a label, or is an analyte analogue, ie a chemical entity having the identical specific binding characteristics as the analyte, and which similarly has been conjugated with a label. In the latter case, it is preferable that the properties of the analyte analogue which influence its solubility or dispersibility in an aqueous liquid sample and its ability to migrate through the moist porous solid phase material should be identical to those of the analyte itself, or at least very closely similar. In this second embodiment, the labelled analyte or analyte analogue will migrate through the porous carrier into the detection zone and bind with the immobilised reagent. Any analyte present in the sample will compete with the labelled reagent in this binding reaction. Such competition will result in a reduction in the amount of labelled reagent binding in the detection zone, and a consequent decrease in the intensity of the signal observed in the detection zone in comparison with the signal that is observed in the absence of analyte in the sample.

In a further alternative embodiment, an analyte or analyte analogue is immobilised in the detection zone, and the labelled reagent is specific for the analyte. If an analyte-containing sample is applied to the device, competition between the immobilised and free analyte reduced the extent to which the labelled reagent may become bound in the detection zone.

In a further embodiment of the present invention, the porous carrier is linked via the macro-porous body to a porous receiving member to which the liquid sample can be applied and from which the sample can permeate into the porous carrier. Preferably, the porous carrier and the macroporous body are contained within a moisture-impermeable casing or housing and the porous receiving member extends out of the housing and can act as a means for permitting a liquid sample to enter the housing and reach the porous carrier. The housing should be provided with means, e.g. appropriately placed apertures, which enable the detection zone of the porous solid phase carrier material (carrying the immobilised unlabelled specific binding reagent) to be observable from outside the housing so that the result of the assay can be observed. If desired, the housing may also be provided with further means which enable a further zone of the porous solid phase carrier material to be observed from outside the housing and which further zone incorporates one or more control reagents which enable an indication to be given as to whether the assay procedure has been completed. Preferably the housing is provided with a removable cap or shroud which can protect the protruding porous receiving member during storage before use. If desired, the cap or shroud can be replaced over the protruding porous receiving member, after sample application, while the assay procedure is being performed.

An important embodiment of the invention is a pregnancy testing device comprising a hollow elongated casing containing a dry porous nitrocellulose carrier which communicates indirectly with the exterior of the casing via a bibulous urine receiving member which protrudes from the casing, the porous nitrocellulose carrier and the sample receiving member being linked via a macroporous body such that any sample reaching the porous carrier must first pass through the macroporous body, the sample receiving member and the macroporous body together acting as a reservoir from which urine is released into the porous carrier, the macroporous body containing a highly-specific anti-hCG antibody bearing a coloured "direct" label, the labelled antibody being freely mobile within the macroporous body and the porous carrier when in the moist state, and in a detection zone on the carrier spatially distant from the macroporous body an highly-specific unlabelled anti-hCG antibody which is permanently immobilised on the carrier material and is therefore not mobile in the moist state, the labelled and unlabelled antibodies having specificities for different hCG epitopes, the casing being constructed of opaque or translucent material incorporating at least one aperture through which the analytical result may be observed, together with a removable and replaceable cover for the protruding bibulous urine receiving member. A fertile period prediction device, essentially as just defined except that the analyte is LH, is an important alternative.

Such devices can be provided as kits suitable for home use, comprising a plurality (e.g. two) of devices individually wrapped in moisture impervious wrapping and packaged together with appropriate instructions to the user.

The porous sample receiving member can be made from any bibulous, porous or fibrous material capable of absorbing liquid rapidly. The porosity of the material can be unidirectional (ie with pores or fibres running wholly or predominantly parallel to an axis of the member) or multi-directional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. It can be advantageous to pre-treat the member with a surface-active agent during manufacture, as this can reduce any inherent hydrophobicity in the member and therefore enhance its ability to take up and deliver a moist sample rapidly and efficiently. Porous sample receiving members can also be made from paper or other cellulosic materials, such as nitro-cellulose. Materials that are now used in the nibs of so-called fibre tipped pens are particularly suitable and such materials can be shaped or extruded in a variety of lengths and cross-sections appropriate in the context of the invention. Preferably the material comprising the porous receiving member should be chosen such that the porous member can be saturated with aqueous liquid within a matter of seconds. Preferably the material remains robust when moist, and for this reason paper and similar materials are less preferred in any embodiment wherein the porous receiving member protrudes from a housing. The liquid must thereafter permeate freely from the porous sample receiving member into the macroporous body.

If present, the "control" zone can be designed merely to convey an unrelated signal to the user that the device has worked. For example, the control zone can be loaded with an antibody that will bind to the labelled reagent, e.g. an "anti-mouse" antibody if the labelled reagent is an antibody that has been derived using a murine hybridoma, to confirm that the sample has permeated the test strip. Alternatively, the control zone can contain an anhydrous reagent that, when moistened, produces a colour change or colour formation, e.g. anhydrous copper sulphate which will turn blue when moistened by an aqueous sample. As a further alternative, a control zone could contain immobilised analyte which will react with excess labelled reagent from the first zone. As the purpose of the control zone is to indicate to the user that the test has been completed, the control zone should be located downstream from the detection zone in which the desired test result is recorded. A positive control indicator therefore tells the user that the sample has permeated the required distance through the test device.

The label can be any entity the presence of which can be readily detected. Preferably the label is a direct label, ie. an entity which, in its natural state, is readily visible either to the naked eye, or with the aid of an optical filter and/or applied stimulation, e.g. UV light to promote fluorescence. For example, minute coloured particles, such as dye sols, metallic sols (e.g. gold), and coloured latex particles, are very suitable. Of these options, coloured latex particles are most preferred. Concentration of the label into a small zone or volume should give rise to a readily detectable signal, e.g. a strongly-coloured area. This can be evaluated by eye, or by instruments if desired.

Indirect labels, such as enzymes, e.g. alkaline phosphatase and horseradish peroxidase, can be used but these usually require the addition of one or more developing reagents such as substrates before a visible signal can be detected. Hence these are less preferred. Such additional reagents can be incorporated in the porous solid phase material or in the macroporous body, or in the sample receiving member if present, such that they dissolve or disperse in the aqueous liquid sample. Alternatively, the developing reagents can be added to the sample before contact with the porous material or the porous material can be exposed to the developing reagents after the binding reaction has taken place.

Coupling of the label to the specific binding reagent can be by covalent bonding, if desired, or by hydrophobic bonding. Such techniques are commonplace in the art, and form no part of the present invention. In the preferred embodiment, where the label is a direct label such as a coloured latex particle, hydrophobic bonding is preferred.

In all embodiments of the invention, it is essential that the labelled reagent migrates with the liquid sample as this progresses to the detection zone. Preferably, the flow of sample continues beyond the detection zone and sufficient sample is applied to the porous carrier material in order that this may occur and that any excess labelled reagent which does not participate in any binding reaction in the detection zone is flushed away from the detection zone by this continuing flow. If desired, an absorbant "sink" can be provided at the distal end of the carrier material. The absorbent sink may comprise, for example, Whatman 3MM chromatography paper, and should provide sufficient absorptive capacity to allow any unbound conjugage to wash out of the detection zone. As an alternative to such a sink it can be sufficient to have a length of porous solid phase material which extends beyond the detection zone.

The presence or intensity of the signal from the label which becomes bound in the detection zone can provide a qualitative or quantitative measurement of analyte in the sample. A plurality of detection zones arranged in series on the porous solid phase material, through which the aqueous liquid sample can pass progressively, can also be used to provide a quantitative measurement of the analyte, or can be loaded individually with different specific binding agents to provide a multi-analyte test.

The immobilised reagent in the detection zone is preferably a highly specific antibody, and more preferably a monoclonal antibody. In the embodiment of the invention involving the sandwich reaction, the labelled reagent is also preferably a highly specific antibody, and more preferably a monoclonal antibody.

Preferably the porous carrier material is in the form of a strip or sheet to which during manufacture of the device, one or more reagents can be applied in spacially distinct zones. During use, the liquid sample is allowed to permeate through the sheet or strip from one side or end to another.

If desired, a device according to the invention can incorporate two or more discrete bodies of porous solid phase carrier material, e.g. separate strips or sheets, each carrying immobilised reagents. These discrete bodies can be arranged in parallel, for example, such that a single application of liquid sample to the device initiates sample flow in the discrete bodies simultaneously. The separate analytical results that can be determined in this way can be used as control results, or if different reagents are used on the different carriers, the simultaneous determination of a plurality of analytes in a single sample can be made. Alternatively, multiple samples can be applied individually to an array of carriers and analysed simultaneously.

The material comprising the porous solid phase is preferably nitrocellulose. This has the advantage that proteinaceous reagents, such as an antibody, in the detection zone can be immobilised firmly without prior chemical treatment. If the porous solid phase material comprises paper, for example, the immobilisation of an antibody in the second zone needs to be performed by chemical coupling using, for example, CNBr, carbonyldiimidazole, or tresyl chloride.

Following the application of the specific biding reagent to the detection zone, the remainder of the porous solid phase material should be treated to block any remaining binding sites elsewhere. Blocking can be achieved by treatment with protein (e.g. bovine serum albumin or milk protein), or with polyvinylalcohol or ethanolamine, or any combination of these agents, for example. Between these process steps the porous solid phase carrier material should be dried.

Preferably the porous solid phase material is nitrocellulose sheet having a pore size of at least about 1 micron, even more preferably of greater than about 5 microns, and yet more preferably about 8–12 microns. Very suitable nitrocellulose sheet having a nominal pore size of up to approximately 12 microns, is available commercially from Schleicher and Schuell GmbH.

Preferably, the nitrocellulose sheet is "backed", e.g. with plastics sheet, to increase its handling strength. This can be manufactured easily by forming a thin layer of nitrocellulose on a sheet of backing material. The actual pore size of the nitrocellulose when backed in this manner will tend to be, lower than that of the corresponding unbacked material.

Alternatively, a pre-formed sheet of nitrocellulose can be tightly sandwiched between two supporting sheets of solid material, e.g. plastics sheets.

It is preferable that the flow rate of an aqueous sample through the porous solid phase material should be such that in the untreated material, aqueous liquid migrates at a rate of 1 cm in not more than 2 minutes, but slower flow rates can be used if desired.

The spatial separation between the macroporous body and the detection zone, and the flow rate characteristics of the porous carrier material, can be selected to allow adequate reaction times during which the necessary specific binding can occur. Further control over these parameters can be achieved by the incorporation of viscosity modifiers (e.g. sugars and modified celluloses) in the sample to slow down the reagent migration.

Preferably, the immobilised reagent in the detection zone is impregnated throughout the thickness of the carrier in the detection zone (e.g. throughout the thickness of the sheet or strip if the carrier is in this form). Such impregnation can enhance the extent to which the immobilised reagent can capture any analyte or labelled reagent, present in the migrating sample.

Reagents can be applied to the porous carrier material in a variety of ways. Various "printing" techniques have previously been proposed for application of liquid reagents to carriers, e.g. micro-syringes, pens using metered pumps, direct printing and ink-jet printing, and any of these techniques can be used in the present context. To facilitate manufacture, the carrier (e.g. sheet) can be treated with the reagents and then subdivided into smaller portions (e.g. small narrow strips each mbodying the required reagent-containing zones) to provide a plurality of identical carrier units.

An assay based on the above principles can be used to determine a wide variety of analytes by choice of appropriate specific binding reagents. The analytes can be, for example, proteins, haptens, immunoglobulins, hormones, polynucleotides, steroids, drugs, infectious disease agents (e.g. of bacterial or viral origin) such as Streptococcus, Neisseria and Chlamydia. Sandwich assays, for example, may be performed for analytes such as hCG (human chorionic gonadotrophin), LH (luteinizing hormone), and infectious disease agents, whereas competition assays, for example, may be carried out for analytes such as E-3-G (estrone-3-glucoronide) and P-3-G (pregnanediol-3-glucoronide).

The determination of the presence (if any) of more than one analyte in sample can have significant clinical utility. For example, the ratio of the levels of apolipoproteins $A_1$ and B can be indicative of susceptibility to coronary heart disease. Similarly, the ratio of the levels of glycated haemoglobin (HbA) to unglycated (HbAo) or total (Hb) haemoglobin can aid in the management of diabetes. Additionally it is possible to configure tests to measure two steroids simultaneously, e.g E-3-G and P-3-G.

The determination of the presence of more than two (ie multiple) analytes in any sample may have significant clinical utility. For example, the detection of the presence of various different sereotypes of one bacterium, or the detection of the presence of soluble serological markers in humans may be useful. By way of example, a multiple analyte test for the detection of the presence of different serotypes of Streptococcus can be prepared for groups A, B, C and D. A cocktail of monoclonal antibodies, each specific for various pathologically important group serotypes, or a polyclonal antiserum raised against a particular Streptococcal group, can be dispensed onto a porous carrier strip as a line extending the width of the strip of approximately 1mm zone length. Multiple lines be dispensed in spatially discrete zones, each zone containing immunochemically reactive component(s) capable of binding the analyte of interest. Following the application of the multiple zones, via a suitable application procedure (eg ink-jet printing, metered pump and pen, airbrush), the remainder of the porous material should be treated with a reagent (eg bovine serum albumin, polyvinylalcohol, ethanolamine) to block any remaining binding sites elsewhere.

By way of example only, some preferred embodiments of the invention will now be described in detail with reference to the accompanying drawings.

Referring to FIG. 1, the device comprises a housing or casing 100 of elongate rectangular form having at one end 101 a portion 102 of reduced cross-sectional area. A cap 103 can be fitted onto portion 102 and can abut against the shoulder 104 at end 101 of the housing. Cap 103 is shown separated from housing 100. Extending beyond end 105 of portion 102 is a porous sample collector 106. When cap 103 is fitted onto portion 102 of the housing, it covers porous sample collector 106. Upper face 107 of housing 100 incorporates two apertures 108 and 109. The housing is constructed of an upper half 110 and a lower half 111.

Referring to FIG. 2, it can be seen that housing 100 is of hollow construction. Porous sample collector 106 extends into housing 100. The inner end 112 of sample collector 106 is recessed to accommodate a macroporous body 113 of plastics material. Aqueous liquid sample applied to collector 106 can pass freely into macroporous body 113, rapidly saturating it. In turn, macroporous body 113 is in liquid permeable contact with a strip of porous carrier material 114. The housing is constructed of an upper half 110 and a lower half 111 and strip 114 overlap to ensure that there is adequate contact between these two components and that a liquid sample applied to sample collector 106 can permeate via macroporous body 113 and into strip 114. Strip 114 extends further into housing 100. To help ensure that no liquid sample reaches Strip 114 without first passing through macroporous body 113, a gap 115 can be left in the housing 100 by arranging for the strip 114 to overlap macroporous body 113 only partially. Strip 114 is "backed" by a supporting strip 116 formed of transparent moisture-impermeable plastics material. Strip 114 extends beyond apertures 108 and 109. Means are provided within housing 100 by webbs 117 and 118 to hold strip 114 firmly in place. In this respect, the internal constructional details of the housing are not a significant aspect of the invention as long as the strip is held firmly in place within the housing, sample collector 106 is firmly retained in the housing, and adequate fluid permeable contact is maintained between sample collector 106, macroporous body 113 and strip 114. The transparent backing strip 116 lies between strip 114 and apertures 108 and 109 and can act as a seal against ingress of moisture from outside the housing 100 via these apertures. If desired, the residual space 119 within the housing can contain moisture-absorbant material, such as silica gel, to help maintain the strip 114 in the dry state during storage. The reagent-containing detection zone in strip 114 is not depicted in FIG. 2, but the zone containing the immobilised unlabelled reagent will lie in the region exposed through Aperture 108 in order that when the device has been used in an assay, the result can be observed through aperture 108. Aperture 109 provides means through which a control zone containing further reagents which may enable the adequate permeation of sample through the strip to be observed.

In operation, the protective cap 103 is removed from the holder and sample collector 106 is exposed to a liquid sample e.g. by being placed in a urine stream in the case of a pregnancy test. After exposing sample collector 106 to the liquid sample for a time sufficient to ensure that the collector 106 is saturated with the sample, the cap 103 can be replaced and the device placed aside by the user for an appropriate period time (e.g. two or three minutes) while the sample permeates test strip 114 to provide the analytical result. After the appropriate time, the user can observe the test strip through apertures 108 and 109 and can ascertain whether the assay has been completed by observing the control zone through aperture 109, and can ascertain the result of the assay by observing the second zone through aperture 108.

During manufacture, the device can be readily assembled from, for example, plastics material with the housing 100 being moulded in two parts (e.g. upper and lower halves 110 and 111) which can be securely fastened together (e.g. by ultrasonic welding) after the sample collector, macroporous body and test strip have been placed within one of the halves and then sandwiched between the two halves. The act of forming this sandwich construction can be used to "crimp" the sample collector macroporous body and test strip together to ensure adequate contact between them. Cap 103 can be moulded as a separate complete item. If desired, apertures 108 and 109 can be provided with transparent inserts which may insure greater security against ingress of extraneous moisture from outside the housing. By providing a tight fit between the end 105 of housing 100 and the protruding sample collector 106, the application of sample to the protruding member will not result in sample entering the device directly and by-passing collector 106. Collector 106 therefore provides the sole route of access for the sample to the strip within the housing, and can deliver sample to the strip in a controlled manner. The device as a whole therefore combines the functions of sampler and analyzer.

By using the test strip materials and reagents as herein described, a device in accordance with FIGS. 1 and 2 can be produced which is eminently suitable for use as a pregnancy test kit or fertile period test kit for use in the home or clinic. The user merely needs to apply a urine sample to the exposed porous member and then (after optionally replacing the cap) can observe the test result through aperture 108 within a matter of a few minutes.

Although described with particular reference to pregnancy tests and fertile period tests, it will be appreciated that the device, as just described, can be used to determine the presence of a very wide variety of analytes if appropriate reagents are incorporated in the test strip. It will be further appreciated that aperture 109 is redundant and may be omitted if the test strip does not contain any control means. Further, the general shape of the housing and cap, both in terms of their length, cross-section and other physical features, can be the subject of considerable variation without departing from the spirit of the invention.

The bibulous sample collector 106 is linked to the macroporous body 113 and test strip 114, backed by the transparent plastics sheet 116, such that liquid can flow in the direction shown by the arrows from the sample collector through the macroporous body and into the porous strip. Test zone 120 incorporates the immobilized specific binding reagent, and control zone 121 contains a reagent to indicate that the sample has permeated a sufficient distance along the test strip.

An aqueous sample deposited in collector 106 can flow into macroporous body 113 and take up labelled reagent therein. The sample can permeate from macroporous body 113 along the length of strip 114 and in so doing will carry the labelled reagent along the strip and through zone 120.

If the desired, eg. for ease of manufacture, the collector 106 need not be recessed to accommodate the macroporous body 113. Instead, these components can simply be placed in an overlapping arrangement, together with the porous strip 114, and pressed together during assembly of the complete device. This will in practice provide a physical arrangement in which the liquid path will be essentially as depicted in FIG. 3.

Embodiment 2

Referring to FIG. 4, the test device comprises a flat rectangular casing 400 incorporating a centrally disposed rectangular aperture 401, adjacent the left hand end 402, and two further apertures 403 and 404 near the mid point of the device and arranged such that apertures 401, 403 and 404 lie on the central longitudinal axis of the device corresponding to line A. Although all three apertures are illustrated as being rectangular, their actual shape is not critical.

Referring to the cross-section seen in FIG. 5, the device is hollow and incorporates within it a macroporous sample receiving member 405 adjacent end 402 of casing 400 and lying directly beneath aperture 401. Sample receiving member 405 is in liquid-conductive contact with one end of a test strip 406 backed by a transparent plastics sheet 407 also contained within casing 400, and which extends to the extreme other end of the casing. The transparent backing sheet 407 is in firm contact with the upper inner surface 408 of casing 400, and provides a seal against apertures 403 and 404 to prevent ingress of moisture or sample into the casing. Although not shown in the drawings, the porous test strip 406 incorporates a test zone and a control zone placed appropriately in relation to apertures 403 and 404, in a manner analogous to that described in Embodiment 1. The macroporous sample receiving member incorporates a labelled reagent which is readily soluble or dispensable in an applied liquid sample.

In operation, an aqueous sample can be applied through aperture 401, e.g. by means of a syringe, to saturate porous receiving member 405 which contains labelled reagent which can be taken up by the sample. Thereafter, the aqueous sample can permeate the test strip and, after an appropriate time, the test result can be observed through apertures 403 and 404.

EXAMPLE

A sheet (1.4 mm thick) of commercially-available, detergent pre-treated, macroporous polyethylene having a pore size of about 100 microns was saturated with an aqueous suspension of blue-coloured latex particles (prepared as described in GB 2204398A) of particle size about 0.4 microns. The latex particles carried an anti-beta LH monoclonal antibody. The solution also contained 3% BSA and 4% sugar. The sheet was then freeze-dried and cut into portions each 6×12 mm, having a liquid capacity of about 50 $\mu$L. These were incorporated in test devices as described above under embodiment 1, with the test strip comprising backed nitrocellulose with an anti-alpha LH monoclonal antibody immobilized in the test zone. The liquid capacity of the "working length" of the test strip between the macroporous body and the detection zone was about 40 $\mu$L.

When a LH-containing urine sample was applied to the device, a positive result showed up as a very clear blue line, with negligible background blue colour being visible in the detection window while the assay was being run.

What is claimed is:

1. An analytical test device suitable for analyzing a liquid sample suspected of containing an analyte, said device comprising the following separate components in sequential fluid communication: (1) a liquid sample application member; (2) a macroporous body positioned to receive liquid sample from said sample application member, said macroporous body including a mobilizable labeled specific binding reagent for binding to analyte in said sample; and (3) a dry porous carrier strip downstream of said macroporous body, said carrier strip including a detection zone comprising an unlabeled immobilized specific binding reagent for binding to said analyte, said mobilizable labeled reagent being freely soluble or dispersible in liquid sample applied to the liquid application member and free to move therewith through the pores of said macroporous body whereby it is transported by said liquid sample from said macroporous body to said detection zone, said macroporous body and carrier strip comprising separate and different materials which overlap at their adjacent ends to provide effective contact between these components to ensure that liquid sample applied to said application member can permeate sequentially through the macroporous body and the carrier strip.

2. The analytical test device according to claim 1, wherein the dry porous carrier strip comprises a chromatographic strip.

3. The analytical test device according to claim 2, wherein the labelled specific binding reagent comprises a specific binding reagent attached to a particulate label.

4. The analytical test device according to claim 3, wherein the particulate label is latex.

5. The analytical test device according to claim 4, wherein the latex comprises particles having a maximum dimension of not greater than about 0.5 micron.

6. The analytical test device according to claim 4, wherein the latex is coloured.

7. The analytical test device according to claim 4, wherein the latex is fluorescent.

8. The analytical test device according to claim 1, wherein the macroporous body comprises plastics material.

9. The analytical test device according to claim 1, wherein the macroporous body has an average pore size of not less than 10 microns.

10. The analytical test device according to claim 3, wherein the macroporous body has a pore size not less than 10 times greater than the maximum particle size of the particulate label.

11. The analytical test device according to claim 1, wherein the porous dry carrier is nitrocellulose.

12. The analytical test device according to claim 11, wherein the nitrocellulose has a pore size of greater than about 1 micron.

13. The analytical test device according to claim 1, wherein the macroporous body is capable of absorbing at least as much of the liquid sample as can be absorbed by the dry porous carrier linking the macroporous body and the detection zone.

14. The analytical test device according to claim 1 wherein the macroporous body and porous carrier are contained within a casing constructed of moisture-impermeable material and the means for applying sample to said macroporous body comprises a sample entry port communicating with the macroporous body, the casing or housing also incorporating means to enable the detection zone to be observable from outside the casing or housing.

15. The analytical device according to claim 1, wherein the porous carrier is linked via the macroporous body to a porous receiving member to which the liquid sample can be applied and from which the sample can permeate into the porous carrier.

16. The analytical device according to claim 15, wherein the porous carrier and the macroporous body are contained within a casing or housing constructed of moisture-impermeable material and the porous receiving member extends out of the casing or housing and can act as a means for permitting a liquid sample to enter the housing and reach the porous carrier, the casing or housing being provided with means which enable the detection zone of the porous carrier to be observable from outside the casing or housing so that the result of the assay can be observed.

17. The analytical device according to claim 16, wherein the casing is provided with means which enable a further zone of the porous carrier to be observed from outside the housing and which further zone incorporates mean which enable an indication to be given as to whether an assay procedure has been completed.

18. The analytical device according to claim 16, comprising a removable cap or shroud which can protect the protruding porous receiving member during storage before use.

19. The analytical test device of claim 1 which comprises a further zone downstream of said detection zone to indicate completion of the assay procedure.

20. A pregnancy testing device for detecting hCG antigen in a urine sample comprising a hollow elongated casing containing a dry porous nitrocellulose carrier which communicates indirectly with the exterior of the casing via a bibulous urine receiving member which protrudes from the casing, the porous nitrocellulose carrier and the sample receiving member being linked via a macroporous body which is different from the dry porous carrier such that any urine sample reaching the porous carrier must first pass through the macroporous body, the sample receiving member and the macroporous body together acting as a reservoir from which urine is released into the porous carrier, the macroporous body containing a specific anti-hCG antibody bearing a coloured particulate label, the labelled antibody being freely mobile within the macroporous body and the porous carrier when in the moist state, and in a detection zone on the carrier spatially distant from the macroporous body a specific unlabelled anti-hCG antibody which is permanently immobilised on the carrier material and is therefore not mobile in the moist state, the labelled and unlabelled antibodies having specificities for different hCG epitopes, the casing being constructed of opaque or translucent material incorporating at least one aperture through which the analytical result may be observed, together with a removable and replaceable cover for the protruding bibulous urine receiving member, said nitrocellulose carrier and macroporous body overlapping at their adjacent ends to provide effective contact between these components to ensure that liquid sample applied to said application member can permeate sequentially through the macroporous body and the carrier strip.

21. A testing device for detecting LH antigen in a urine sample comprising a hollow elongated casing containing a dry porous nitrocellulose carrier which communicates indirectly with the exterior of the casing via a bibulous urine receiving member which protrudes from the casing, the porous nitrocellulose carrier and the sample receiving member being linked via a macroporous body which is different from the dry porous carrier such that any urine sample reaching the porous carrier must first pass through the macroporous body, the sample receiving member and the macroporous body together acting as a reservoir from which urine is released into the porous carrier, the macroporous body containing a specific anti-LH antibody bearing a coloured particulate label, the labelled antibody being freely mobile within the macroporous body and the porous carrier when in the moist state, and in a detection zone on the carrier spatially distant from the macroporous body a specific unlabelled anti-LH antibody which is permanently immobilised on the carrier material and is therefore not mobile in the moist state, the labelled and unlabelled antibodies having specificities for different LH epitopes, the casing being constructed of opaque or translucent material incorporating at least one aperture through which the analytical result may be observed, together with a removable and replaceable cover for the protruding bibulous urine receiving member, said nitrocellulose carrier and macroporous body overlapping at their adjacent ends to provide effective contact between these components to ensure that liquid sample applied to said application member can permeate sequentially through the macroporous body and the carrier strip.

* * * * *